US008500947B2

(12) United States Patent  (10) Patent No.: US 8,500,947 B2
Abuzaina  (45) Date of Patent: Aug. 6, 2013

(54) SPEEDING CURE RATE OF BIOADHESIVES

(75) Inventor: Ferass Abuzaina, Shelton, CT (US)

(73) Assignee: Covidien LP, Mansfield, MA (US)

( * ) Notice: Subject to any disclaimer, the term of this patent is extended or adjusted under 35 U.S.C. 154(b) by 540 days.

(21) Appl. No.: 12/258,503

(22) Filed: Oct. 27, 2008

(65) Prior Publication Data

US 2009/0131621 A1  May 21, 2009

Related U.S. Application Data

(60) Provisional application No. 60/988,209, filed on Nov. 15, 2007.

(51) Int. Cl.
C09J 4/00 (2006.01)

(52) U.S. Cl.
USPC ............. 156/331.7; 156/330.9; 156/331.14; 156/331.4; 524/589; 524/590; 528/59; 528/61; 528/62; 528/63; 528/64

(58) Field of Classification Search
USPC .............. 528/59, 61, 62, 63, 64; 524/589, 524/590; 156/330.9, 331.1, 331.4, 331.7
See application file for complete search history.

(56) References Cited

U.S. PATENT DOCUMENTS

| 2,890,208 | A | 6/1959 | Young et al. |
| 2,990,379 | A | 6/1961 | Young |
| 3,063,967 | A | 11/1962 | Schultz |
| 3,169,945 | A | 2/1965 | Hostettler et al. |
| 3,391,126 | A | 7/1968 | Baggett et al. |
| 3,463,762 | A | 8/1969 | Trischler |
| 3,631,138 | A * | 12/1971 | Peters ................... 524/871 |
| 3,645,941 | A | 2/1972 | Snapp et al. |
| 3,666,724 | A | 5/1972 | Hostettler |
| 3,741,941 | A | 6/1973 | Ashe |
| 3,773,595 | A | 11/1973 | Burba et al. |
| 3,795,701 | A | 3/1974 | Jenkins et al. |
| 3,903,232 | A | 9/1975 | Wood et al. |
| 3,912,692 | A | 10/1975 | Casey et al. |
| 4,052,988 | A | 10/1977 | Doddi et al. |
| 4,057,535 | A | 11/1977 | Lipatova et al. |
| 4,080,969 | A | 3/1978 | Casey et al. |
| 4,118,470 | A | 10/1978 | Casey et al. |
| 4,323,491 | A | 4/1982 | Veselovsky et al. |
| 4,359,049 | A | 11/1982 | Redl et al. |
| 4,361,055 | A | 11/1982 | Kinson |
| 4,425,472 | A | 1/1984 | Howard et al. |
| 4,440,789 | A | 4/1984 | Mattei et al. |
| 4,503,216 | A | 3/1985 | Fagerburg et al. |
| 4,623,709 | A | 11/1986 | Bauriedel |
| 4,624,256 | A | 11/1986 | Messier et al. |
| 4,632,975 | A | 12/1986 | Cornell et al. |
| 4,643,191 | A | 2/1987 | Bezwada et al. |
| 4,655,777 | A | 4/1987 | Dunn |
| 4,663,429 | A | 5/1987 | Murai et al. |
| 4,698,375 | A | 10/1987 | Dorman |
| 4,740,534 | A | 4/1988 | Matsuda et al. |
| 4,743,632 | A | 5/1988 | Marinovic |
| 4,804,691 | A | 2/1989 | English et al. |
| 4,822,685 | A | 4/1989 | Perez |
| 4,826,945 | A | 5/1989 | Cohn et al. |
| 4,829,099 | A | 5/1989 | Fuller |
| 4,874,368 | A | 10/1989 | Miller et al. |
| 4,978,336 | A | 12/1990 | Capozzi et al. |
| 4,979,942 | A | 12/1990 | Wolf et al. |
| 4,994,542 | A | 2/1991 | Matsuda et al. |
| 5,047,048 | A | 9/1991 | Bezwada et al. |
| 5,065,752 | A | 11/1991 | Sessions et al. |
| 5,076,807 | A | 12/1991 | Bezwada et al. |
| 5,080,665 | A | 1/1992 | Jarrett et al. |
| 5,085,629 | A | 2/1992 | Goldberg et al. |
| 5,100,433 | A | 3/1992 | Bezwada et al. |
| 5,166,300 | A | 11/1992 | Rumon et al. |
| 5,169,720 | A | 12/1992 | Braatz et al. |
| 5,173,301 | A | 12/1992 | Itoh |
| 5,175,228 | A | 12/1992 | Wang et al. |
| 5,225,521 | A | 7/1993 | Spinu |
| 5,256,765 | A | 10/1993 | Leong |
| 5,266,323 | A | 11/1993 | Guthrie et al. |
| 5,266,608 | A | 11/1993 | Katz et al. |
| 5,290,853 | A | 3/1994 | Regan et al. |
| 5,296,518 | A | 3/1994 | Grasel et al. |
| 5,334,626 | A | 8/1994 | Lin |
| 5,368,563 | A | 11/1994 | Lonneman et al. |
| 5,457,141 | A | 10/1995 | Matsuda et al. |
| 5,462,536 | A | 10/1995 | Braatz et al. |
| 5,578,662 | A | 11/1996 | Bennett et al. |
| 5,703,158 | A | 12/1997 | Duan et al. |
| 5,717,030 | A | 2/1998 | Dunn et al. |
| 5,791,352 | A | 8/1998 | Reich et al. |
| 5,948,472 | A | 9/1999 | Lawrie |
| 5,990,237 | A | 11/1999 | Bentley et al. |
| 6,071,530 | A | 6/2000 | Polson |
| 6,162,241 | A | 12/2000 | Coury et al. |
| 6,207,767 | B1 | 3/2001 | Bennett et al. |
| 6,217,894 | B1 | 4/2001 | Sawhney et al. |
| 6,256,765 | B1 | 7/2001 | Krimmer |
| 6,261,544 | B1 | 7/2001 | Coury et al. |

(Continued)

FOREIGN PATENT DOCUMENTS

EP 0077192 A2 4/1983
EP 0390481 10/1990

(Continued)

OTHER PUBLICATIONS

European Search Report for EP 08253645.9-2115 date of completion is Feb. 25, 2009 (5 pages).
Ferreira P et al. "Development of a Biodegradable Bioadhesive containing Urethane Groups", Journal of Materials Science: Materials in Medicine, Kluwer Academic Publishers, BO, vol. 19, No. 1, Jun. 21, 2007, pp. 111-120, XP019575568.
Ferreira et al. "Modification of the Biopolymer Castor Oil with Free Isocyanate Groups to be Applied as Bioadhesive" International Journal of Biological Macromolecules, Elsevier BV, NL, vol. 40, No. 2, Jan. 4, 2007, pp. 144-152, XP005821929.

Primary Examiner — Michael L Leonard

(57) ABSTRACT

The present disclosure provides compositions having reduced viscosity which may be used as adhesives or tissue sealants, and includes methods for speeding the cure rate of such compositions.

13 Claims, No Drawings

U.S. PATENT DOCUMENTS

| | | |
|---|---|---|
| 6,290,729 B1 | 9/2001 | Slepian et al. |
| 6,339,130 B1 | 1/2002 | Bennett et al. |
| 6,352,710 B2 | 3/2002 | Sawhney et al. |
| 6,395,112 B1 | 5/2002 | Sitzmann et al. |
| 6,395,823 B1 | 5/2002 | Brink et al. |
| 6,423,810 B1 | 7/2002 | Huang et al. |
| 6,495,127 B1 | 12/2002 | Wallace et al. |
| 6,527,749 B1 | 3/2003 | Roby et al. |
| 6,566,406 B1 | 5/2003 | Pathak et al. |
| 6,582,713 B2 | 6/2003 | Newell et al. |
| 6,702,731 B2 | 3/2004 | Milbocker |
| 6,894,140 B2 | 5/2005 | Roby |
| 2003/0012734 A1 | 1/2003 | Pathak et al. |
| 2003/0032734 A1 | 2/2003 | Roby |
| 2003/0108511 A1 | 6/2003 | Sawhney |
| 2003/0135238 A1 | 7/2003 | Milbocker |
| 2004/0023842 A1 | 2/2004 | Pathak et al. |
| 2004/0068078 A1 | 4/2004 | Milbocker |
| 2004/0198901 A1 | 10/2004 | Graham et al. |
| 2005/0004661 A1 | 1/2005 | Lewis et al. |
| 2005/0069573 A1 | 3/2005 | Cohn et al. |
| 2005/0070913 A1 | 3/2005 | Milbocker et al. |
| 2005/0129733 A1 | 6/2005 | Milbocker et al. |
| 2005/0147647 A1 | 7/2005 | Glauser et al. |
| 2005/0266086 A1 | 12/2005 | Sawhney |
| 2007/0128152 A1 | 6/2007 | Hadba et al. |
| 2007/0135605 A1 | 6/2007 | Hadba et al. |
| 2007/0135606 A1 | 6/2007 | Belcheva et al. |

FOREIGN PATENT DOCUMENTS

| | | |
|---|---|---|
| EP | 482467 | 4/1992 |
| EP | 0488629 | 6/1992 |
| EP | 0693294 | 1/1996 |
| EP | 0727230 | 8/1996 |
| EP | 0301516 | 2/1998 |
| EP | 1391205 A1 | 2/2004 |
| FR | 1351368 | 12/1963 |
| GB | 887180 | 1/1962 |
| GB | 1143309 | 2/1969 |
| GB | 1187362 | 4/1970 |
| JP | 6263850 | 9/1994 |
| JP | 2002060341 | 2/2002 |
| WO | WO 8905830 | 6/1989 |
| WO | WO 9409048 | 4/1994 |
| WO | WO 2004039323 | 5/2004 |

* cited by examiner

SPEEDING CURE RATE OF BIOADHESIVES

CROSS-REFERENCE TO RELATED APPLICATIONS

This application claims the benefit of and priority to U.S. Provisional Patent Application No. 60/988,209, filed Nov. 15, 2007, the entire disclosure of which is incorporated by reference herein.

BACKGROUND

1. Technical Field

The present disclosure relates to compositions suitable for application in situ, including for use as tissue adhesives and/or tissue sealants.

2. Background of Related Art

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, cyanoacrylate adhesives can have a high flexural modulus which can limit their usefulness. Another type of tissue sealant that is currently available utilizes components derived from bovine and/or human sources. For example, fibrin sealants are available. However, as with any natural material, variability in the material can be observed.

It would be desirable to provide a fully synthetic biological adhesive or sealant that is flexible, biocompatible and highly consistent in its properties.

SUMMARY

The present disclosure provides compositions having reduced viscosity which may be used as adhesives or tissue sealants, and includes methods for speeding the cure rate of such compositions. In embodiments, a method of the present disclosure includes contacting at least one isocyanate-terminated component with a dilute solution including at least one amine at a concentration of from about 0.01 weight percent to about 0.5 weight percent of the solution, and allowing the at least one isocyanate-terminated component and the at least one amine to react in situ thereby forming a biocompatible composition. In embodiments, the at least one isocyanate-terminated component may be of the formula:

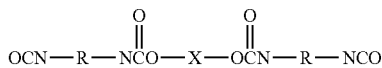

wherein X is a polyether, a polyester or a polyether-ester group, and R is an aliphatic or aromatic group.

In embodiments, the ratio of the amine to the at least one isocyanate-terminated component may be from about 1:10 to about 10:1 w/w.

In embodiments, the at least one isocyanate-terminated component and the at least one amine form the biocompatible composition within from about 1 second to about 5 minutes after contact.

Adhesives and sealants made with these compositions are also provided. The composition thus formed may exhibit a lap shear of from about 0.8 kg to about 2 kg.

In other embodiments, a method of the present disclosure may include contacting at least one isocyanate-terminated component with a dilute solution including at least one amine such as bis(3-aminopropyl)amine, spermine, polyetheramine, trilysine, ethylenediamine, N-ethylethylenediamine, N,N'-diethylethylenediamine, butane-1,4-diamine, pentane-1,5-diamine, hexane-1,6-diamine, phenylene diamine, and combinations thereof having a molecular weight of from about 50 g/mol to about 500 g/mol, at a concentration of from about 0.01 percent by weight to about 0.5 percent by weight of the solution, and allowing the at least one isocyanate-terminated polyurethane and the at least one amine to react in situ thereby forming a biocompatible composition.

DETAILED DESCRIPTION

The present disclosure relates to compositions which are biocompatible, non-immunogenic and biodegradable. As used herein, a "composition" of the present disclosure includes the composition by itself or with optional additives and/or additional compounds. The compositions can be applied to living tissue and/or flesh of animals, including humans.

While certain distinctions may be drawn between the usage of the terms "flesh" and "tissue" within the scientific community, the terms are used interchangeably herein as referring to a general substrate upon which those skilled in the art would understand the present composition to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic and/or ascite tissue.

In embodiments the compositions may be utilized as tissue adhesives and/or tissue sealants. The compositions can be employed to adhere tissue edges, seal air/fluid leaks in tissues, adhere medical devices, for example implants, to tissue, and for tissue augmentation such as sealing or filling voids or defects in tissue.

The compositions of the present disclosure include a first component and a second component. The second component includes at least one amine group and is selected to increase the curing rate of the composition upon application in situ.

In embodiments, the first component utilized in forming compositions of the present disclosure may include isocyanate-functional polymers. Any monomer, oligomer, or polymer that may be functionalized with an isocyanate group may be utilized as the first component. In embodiments a first component may be based upon an isocyanate-functional polyether, polyester, or polyether-ester group.

Suitable polyethers which may be utilized in forming the first component are within the purview of those skilled in the art and include, for example, polyethylene glycol, polypropylene glycol, polybutylene glycol, polytetramethylene glycol, polyhexamethylene glycol, copolymers thereof, and combinations thereof. In embodiments a suitable polyether may be polyethylene glycol.

Suitable polyesters which may be utilized in forming the first component are within the purview of those skilled in the art and include, for example, trimethylene carbonate, ε-caprolactone, p-dioxanone, glycolide, lactide, 1,5-dioxepan-2-one, polybutylene adipate, polyethylene adipate, polyethylene terephthalate, and combinations thereof.

In addition, as noted above, the first component may include a poly(ether-ester) block. Any suitable poly(ether-ester) block within the purview of those skilled in the art may be utilized. These macromers may include an aliphatic diacid linking two dihydroxy compounds (sometimes referred to herein as a "poly(ether-ester) macromer"). Up to ten repeats of the poly(ether-ester) macromer may be present.

Suitable aliphatic diacids which may be utilized in forming the poly(ether-ester) macromer include, for example, aliphatic diacids having from about 2 to about 10 carbon atoms. Suitable diacids include, but are not limited to, sebacic acid, azelaic acid, suberic acid, pimelic acid, adipic acid, glutaric acid, succinic acid, malonic acid, oxalic acid, and combinations thereof.

Suitable dihydroxy compounds which may be utilized in forming the poly(ether-ester) macromer include, for example, polyols including polyalkylene oxides, polyvinyl alcohols, and the like. In some embodiments, the dihydroxy compounds can be a polyalkylene oxide such as polyethylene oxide ("PEO"), polypropylene oxide ("PPO"), block or random copolymers of polyethylene oxide (PEO) and polypropylene oxide (PPO), and combinations thereof.

In one embodiment, a polyethylene glycol ("PEG") may be utilized as the dihydroxy compound. It may be desirable to utilize a PEG with a molecular weight of from about 200 g/mol to about 10000 g/mol, in embodiments from about 400 g/mol to about 900 g/mol. Suitable PEGs include those commercially available from a variety of sources under the designations PEG 200, PEG 400, PEG 600 and PEG 900.

Any method may be used to form the poly(ether-ester) macromer. In some embodiments, the poly(ether-ester) macromer may be formed by combining adipoyl chloride with a PEG such as PEG 600 and pyridine in a suitable solvent, such as tetrahydrofuran (THF). The solution may be held at a suitable temperature, from about −70° C. to about 25° C., for a period of time of from about 4 hours to about 18 hours, after which the reaction mixture may be filtered to remove the precipitated pyridine hydrochloride by-product and the resulting poly(ether-ester) macromer, here a PEG/adipate compound. The resulting poly(ether-ester) macromer may be obtained from the solution by the addition of ether or petroleum ether, and collected by suitable means which can include filtration. Other methods suitable for producing the present compounds are within the purview of those skilled in the art.

Other examples of suitable poly(ether-ester) blocks which may be utilized include, but are not limited to, polyethylene glycol-polycaprolactone, polyethylene glycol-polylactide, polyethylene glycol-polyglycolide, and various combinations of the individual polyethers and polyesters described herein. Additional examples of suitable poly(ether-ester) blocks include those disclosed in U.S. Pat. No. 5,578,662 and U.S. Patent Application No. 2003/0135238, the entire disclosures of each of which are incorporated by reference herein.

In embodiments, the resulting poly(ether-ester) macromer may be of the following formula:

$$HO-(R-A)_n-R-OH \quad (I)$$

wherein A is a group derived from an aliphatic diacid; R can be the same or different at each occurrence and may include a group derived from a dihydroxy compound; and n may be from about 1 to about 10. In some embodiments, the A group can be derived from adipic acid, and R can be derived from a polyethylene glycol having a molecular weight of from about 200 g/mol to about 1000 g/mol, in embodiments from about 400 g/mol to about 800 g/mol, in embodiments about 600 g/mol.

The molecular weight and viscosity of these compounds may depend on a number of factors such as the particular diacid used, the particular dihydroxy compound used, and the number of repeat units present. Generally, the viscosity of these compounds may be from about 300 to about 10,000 cP at 25° C. and a shear rate of 20.25 sec$^{-1}$.

In embodiments, the polyether, polyester, or polyether-ester group may be endcapped with functional groups. Methods for endcapping the polyether, polyester, or poly(ether-ester) to provide a reactive end group are within the purview of those skilled in the art. While the present disclosure discusses endcapping with isocyanate groups in detail, the first component of the present disclosure may also be endcapped with other amine reactive end groups, for example, isothiocyanates, diimidazoles, imidoesters, hydroxysuccinimide esters, aldehydes, combinations thereof, and the like.

In embodiments, the first component may be endcapped with an isocyanate to produce a diisocyanate-functional compound. Suitable isocyanates for endcapping the polyether, polyester or poly(ether-ester) block include aromatic, aliphatic and alicyclic isocyanates. Examples include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenyl isocyanate), 4,4'-methylenebis(phenyl isocyanate), or tetramethylxylylene diisocyanate; aliphatic diisocyanates such as tetramethylene diisocyanate, hexamethylene diisocyanate, dimethyl diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate, or commercially available materials including those sold under the DESMODURS® name from Bayer Material Science.

Methods for endcapping the polyether, polyester, or poly (ether-ester) macromer with a diisocyanate are within the purview of those skilled in the art. For example, the polyether, polyester, or poly(ether-ester) macromer may be combined with a suitable diisocyanate at a molar ratio of polyether, polyester or poly(ether-ester) macromer to diisocyanate of from about 1:2 to about 1:6, in embodiments from about 1:3 to about 1:5, in other embodiments about 1:4, and heated to a suitable temperature of from about 55° C. to about 75° C., in embodiments from about 60° C. to about 70° C., in other embodiments about 65° C. It may be desirable to agitate the components utilizing means within the purview of those skilled in the art, including stirring, mixing, blending, sonication, combinations thereof, and the like.

In some embodiments, the endcapping reaction may occur under an inert atmosphere, for example, under nitrogen gas. Catalysts, including alkoxides, stannous octoate, dibutyltin dilaurate, 1,4-diazabicyclo[2.2.2]octane (DABCO), combinations thereof, and the like, may be utilized in some embodiments to increase the rate of the endcapping reaction.

It may be desirable, in embodiments, to utilize an excess of diisocyanate in carrying out the reaction. The use of an excess of diisocyanate may suppress the polymerization reaction, thereby permitting one to tailor the resulting molecular weight of the resulting isocyanate functionalized first component. In some embodiments the resulting diisocyanate-functional compound may then be obtained by hot extraction with petroleum ether.

Thus, in embodiments, suitable macromers which may be utilized as the first component of a composition of the present disclosure may include, but are not limited to, those of the following formula:

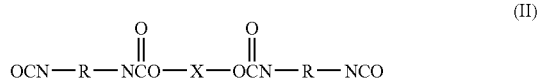

(II)

wherein X is a polyether, a polyester or a polyether-ester as described above; and R is an aromatic, aliphatic, or alicyclic group as described above.

The macromers described above as suitable for use as a first component in a composition of the present disclosure may have a molecular weight of from about 1000 g/mol to about 20000 g/mol, in embodiments from about 1500 g/mol to about 10000 g/mol. The viscosity of the first component may be from about 10 cP to about 500,000 cP, in embodiments from about 100 cP to about 200,000 cP, typically from about 200 cP to about 100,000 cP.

It should be understood that more than one different polyether, polyester, or poly(ether-ester) macromer can be endcapped in a single reaction. The resulting product will be a mixture of diisocyanate-functional compounds of formula II shown above.

The NCO content of the diisocyanate-functional compound can vary from about 3% to about 6%, in embodiments from about 3.5% to about 5%.

The second component of a composition of the present disclosure includes at least one amine group. Suitable compounds containing at least one amine group which may be utilized as the second component include, for example, primary amines such as bis(3-aminopropyl)amine, spermine, polyetheramine (including JEFFAMINE® polyetheramines), and trilysine, as well as low molecular weight diamines, such as ethylenediamine, N-ethylethylenediamine, N,N'-diethylethylenediamine, butane-1,4-diamine, pentane-1,5-diamine, hexane-1,6-diamine, phenylene diamine, and combinations thereof. In embodiments, the compound possessing the amine group may have a low molecular weight of less than about 5000 g/mol, in embodiments from about 50 g/mol to about 500 g/mol, in other embodiments from about 100 g/mol to about 300 g/mol.

In embodiments, the second component may be in a dilute solution. Suitable solvents which may be utilized to form this dilute solution include any biocompatible solvents within the purview of those skilled in the art which will not interfere with the reaction of the amine groups of the second component with the isocyanate-functional groups of the first component. Suitable solvents which may be utilized include, for example, polar solvents such as water, ethanol, triethylene glycol, dimethyl sulfoxide (DMSO), glymes (such as diglyme, triglyme, tetraglyme, and the like), polyethylene glycols, methoxy-polyethylene glycols, dimethylformamide, dimethylacetamide, gamma-butyrolactone, N-methylpyrrolidone (NMP), ketones such as methyl ethyl ketone, cyclohexanone, diethylene glycol monoethyl ether acetate, diethylene glycol monobutyl ether acetate, diethylene glycol monomethyl ether, diethylene glycol monoethyl ether, diethylene glycol monobutyl ether, diethylene glycol monoisobutyl ether, diisobutyl ketone, diacetone alcohol, ethyl amyl ketone, ethyl lactate, and the like. In other embodiments, solvents such as tetrahydrofuran, ethyl acetate, isopropyl acetate, butyl acetate, isopropanol, butanol, acetone, and the like, may be utilized. In embodiments, combinations of any of the foregoing solvents may be utilized to form a dilute solution.

A solvent may be mixed with the second component so that the second component is at a concentration of from about 0.01 weight percent to about 0.5 weight percent of the dilute solution, in embodiments from about 0.05 weight percent to about 0.1 weight percent of the dilute solution.

The amount of solvent used will depend on a number of factors including the particular second component employed and the intended end use of the composition.

In accordance with the present disclosure, the rate of curing of a composition of the present disclosure may be tailored by controlling the concentration of the second component in the dilute solution. Generally, a faster cure time may be observed at a higher concentration of the second component in the dilute solution than the rate observed for the same second component at a lower concentration. Compositions of the present disclosure may cure from about 1 second to about 5 minutes after the two components are contacted and applied to tissue, in embodiments from about 30 seconds to about 2.5 minutes after contact.

Where the first component includes isocyanate functionality and the dilute solution containing the second component contains hydroxyl groups, the first component and second component in dilute solution may be advantageously mixed immediately prior to use to avoid undesired pre-gelling.

In embodiments, the second component may be mixed with the first component at a ratio of from about 1:10 to about 10:1 w/w, in embodiments, at a ratio of from about 5:1 to about 1:1 w/w.

A variety of optional ingredients may also be added to the compositions of the present disclosure including, but not limited to, surfactants, antimicrobial agents, colorants, preservatives, imaging agents e.g., iodine or barium sulfate, or fluorine, or medicinal agents. In some embodiments, the present compositions may optionally contain one or more bioactive agents. The term "bioactive agent", as used herein, is used in its broadest sense and includes any substance or mixture of substances that have clinical use. Consequently, bioactive agents may or may not have pharmacological activity per se, e.g., a dye. Alternatively, a bioactive agent could be any agent which provides a therapeutic or prophylactic effect, a compound that affects or participates in tissue growth, cell growth, and/or cell differentiation, a compound that may be able to invoke a biological action such as an immune response, or could play any other role in one or more biological processes.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Suitable antimicrobial agents which may be included as a bioactive agent in the present compositions include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine or rh-lactoferrin and lactoferricin B may be included as a bioactive agent in the present compositions.

Other bioactive agents which may be included as a bioactive agent in the present compositions include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anticancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present compositions include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

Naturally occurring polymers, including proteins such as collagen and derivatives of various naturally occurring polysaccharides such as glycosaminoglycans, can optionally be incorporated into the compositions the bioactive agent of the present disclosure.

A single bioactive agent may be utilized to form the present compositions or, in alternate embodiments, any combination of bioactive agents may be utilized to form the present compositions.

Due to the presence of the functionalized first and second components described above, the present compositions cross-link to form a gel matrix that serves as an excellent tissue adhesive or sealant upon administration to tissue. Normally, the cross-linking reaction may be conducted at temperatures of from about 20° C. to about 40° C., in embodiments from about 25° C. to about 37° C. The exact reaction conditions for achieving cross-linking of the compositions of the present disclosure depend upon a variety of factors, including the functionality of the components, the degree of endcapping, the degree of functionalization, the presence of a catalyst, the particular solvent, if any, and the like.

Where the composition of the present disclosure is intended for delivery of a drug or protein, the amounts of the functionalized first and second components can be adjusted to promote the initial retention of the drug or polymer in the bioabsorbable composition and its subsequent release. Methods and means for making such adjustments will be readily apparent to those skilled in the art.

The first component and the dilute solution including the second component utilized to form an adhesive and/or sealant of the present disclosure may be combined utilizing any method within the purview of those skilled in the art, including mixing, blending, dripping, brushing, and the like, or any other direct manipulation of the compositions on the tissue surface, or spraying of the compositions onto the surface. In open surgery, application by hand, forceps or the like is contemplated. In endoscopic surgery, the compositions can be delivered through the cannula of a trocar, and spread at the site by any device known in the art.

For example, in some embodiments the isocyanate-functional first component and the second component in dilute solution may be combined using mixing with a simple device such as a spatula. In other embodiments, the first component and the second component in dilute solution may be combined by simply placing the two components into a first syringe and expelling the contents of the first syringe into a second syringe, followed by expelling the contents of the second syringe into the first syringe, and repeating this process between the two syringes until the components are mixed.

Thus, in some embodiments, the first component and the second component in dilute solution may be combined prior to administration. This may be advantageous where the compositions of the present disclosure are to be utilized as a void filler or sealant to fill a defect in an animal's body, in order to more precisely control the conditions and extent of cross-linking. For example, it may be desirable to partially cross-link the composition prior to use to fill a void in animal tissue. In such a case composition of the present disclosure can be applied to the void or defect and allowed to set, thereby filling the void or defect.

In other embodiments, the first component may be combined with the second component in dilute solution at the time of administration. One example includes keeping the first component separate from the second component and spraying the individual ingredients in a consecutive manner onto the same location, thereby allowing the two ingredients to mix and form a bond in situ. Another example includes keeping the first component separate from the second component and spraying the two ingredients simultaneously through the same device such as a sprayer or nozzle, thereby allowing the two ingredients to mix while being sprayed onto tissue, at which time they will form a bond in situ.

Methods for combining the two components at the time of administration are within the purview of those skilled in the art and include, for example, dispensing the two components from a conventional adhesive dispenser, which typically provides mixing of the first and second components prior to the dispenser. Such dispensers are disclosed, for example, in U.S. Pat. Nos. 4,978,336, 4,361,055, 4,979,942, 4,359,049, 4,874,368, 5,368,563, and 6,527,749, the entire disclosures of each of which are incorporated by reference herein.

The compositions of the present disclosure can be used for a number of different human and animal medical applications including, but not limited to, wound closure (including surgical incisions and other wounds). Adhesives may be used to bind tissue together either as a replacement of, or as a supplement to, sutures, staples, clamps, tapes, bandages, and the like. Use of the present compositions can eliminate or substantially reduce the number of sutures normally required during current practices, and eliminate the subsequent need for removal of staples and certain types of sutures. The compositions described herein can thus be particularly suitable for use with delicate tissues where sutures, clamps or other conventional tissue closure mechanisms may cause further tissue damage. For example, the compositions of the present disclosure may be used to seal or adhere delicate tissue together, such as lung tissue, in place of conventional tools that may cause mechanical stress. The present compositions can also be used to seal air and/or fluid leaks in tissue as well as to prevent post-surgical adhesions and to fill voids and/or defects in tissue.

To effectuate the joining of two tissue edges, the two edges may be approximated, and a composition of the present disclosure may be applied to the two approximated edges. The composition crosslinks rapidly, generally taking less than one minute. Compositions of the present disclosure can thus be applied to the wound and allowed to set, thereby closing the wound.

The compositions described herein can also be used as sealants. When used as a sealant, a composition of the present disclosure can be used in surgery to prevent or inhibit bleeding or fluid leakage both during and after a surgical procedure. It can also be applied to prevent air leaks associated with pulmonary surgery. Compositions herein may be applied directly to the desired area in at least an amount sufficient to seal off any defect in the tissue and seal off any fluid or air movement. The compositions may also be used to prevent or control blood or other fluid leaks at suture or staple lines.

The present compositions also can be used to attach skin grafts and position tissue flaps during reconstructive surgery. Alternatively, the present compositions can be used to close tissue flaps in periodontal surgery.

In another embodiment, the present disclosure is directed to a method for using compositions of the present disclosure to adhere a medical device to tissue. Suitable medical devices include implants. Other medical devices include, but are not limited to, pacemakers, stents, shunts and the like. Generally, for adhering a device to the surface of animal tissue, a composition of the present disclosure can be applied to the device, to the tissue surface or to both. The device and tissue surface are then brought into contact with the present composition therebetween. Once the composition crosslinks and sets, the device and tissue surface are effectively adhered to each other.

The present compositions can also be used to prevent post surgical adhesions. In such an application, a composition of the present disclosure is applied and cured to form a layer on surfaces of internal tissues in order to prevent the formation of adhesions at a surgical site during the healing process.

The resulting bioabsorbable compositions have a number of advantageous properties. The bioabsorbable compositions of the present disclosure are safe, possess enhanced adherence to tissue, are biodegradable, have enhanced hemostatic potential, have low cost, and are easy to prepare and use. By varying the selection of the compounds utilized to form the bioabsorbable composition, the strength and elasticity of the bioabsorbable composition can be controlled, as can the gelation time.

Adhesives and/or sealants formed with compositions of the present disclosure possess excellent strength and similar physical properties. For example, when applied to porcine tissue and tested for lap shear, i.e., the pull force needed to separate two pieces of tissue, compositions of the present disclosure exhibit an average lap shear of from about 0.8 kg to about 2 kg, in embodiments from about 1 kg to about 1.5 kg, in other embodiments about 1.4 kg within about 2 minutes after application to tissue. Adhesives and/or sealants formed with compositions of the present disclosure form rapidly, in embodiments from about 1 second to about 5 minutes, in other embodiments from about 30 seconds to about 2 minutes, after contacting the first component with the second component.

The compositions herein rapidly form a compliant gel matrix, which insures stationary positioning of tissue edges or implanted medical devices in the desired location and lowers overall required surgical/application time. The resulting composition exhibits little or no swelling upon gel matrix formation, and therefore retains the positional integrity of the aligned tissue edges and/or location of a medical device. The composition forms strong cohesive bonds. It exhibits excellent mechanical performance and strength, while retaining the necessary pliability to adhere living tissue. This strength and pliability allows a degree of movement of tissue without shifting the surgical tissue edge.

The following Examples are being submitted to illustrate embodiments of the present disclosure. These Examples are intended to be illustrative only and are not intended to limit the scope of the present disclosure. Also, parts and percentages are by weight unless otherwise indicated.

EXAMPLE 1

An isocyanate-functional first component was prepared as follows: PEG 600 (commercially available from Sigma Aldrich, St. Louis, Mo.) was heated to about 65° C. for about 3 hours while bubbling nitrogen into the PEG 600. About 275 grams of the PEG 600 was then dissolved in about 730 grams of tetrahydrofuran (THF). About 53 grams of pyridine was dissolved in about 200 grams of THF. The pyridine solution was then combined with the PEG 600-THF solution. About 56 grams of adipoyl chloride was dissolved in about 653 ml of THF. The adipoyl chloride solution was added dropwise to the other THF solution containing both PEG 600 and pyridine at a rate of about 100 drops per minute until completely added. The solution remained under stirring for about 2 hours. The material was then filtered to get rid of the pyridine-hydrochloride salts and the filtrate was concentrated using a ROTAVAPOR® rotary evaporator. The solution was then precipitated in about 2.5 liters of ethyl ether.

The precipitate, PEG 600-Adipate (polylol), was dried under a vacuum. About 195 of the PEG-Adipate was then combined with about 100 grams of about 80% toluene 2,4-diisocyanate (TDI) from Sigma Aldrich. The mixture was heated to about 65° C. while mixing at about 150 revolutions per minute (rpm) for about 4 hours under static nitrogen. The resulting product was cleaned from excess (unreacted) TDI by adding petroleum ether and mixing at about 300 rpm for about 20 minutes followed by decanting (this step was repeated at least three times). The resulting material, TDI functionalized PEG 600 adipate, was placed under a vacuum and dried overnight.

Finally, trimethylolpropane (TMP) obtained from Sigma-Aldrich was dried by heating to about 110° C. for about 2 hours while bubbling dry nitrogen in the TMP. About 100 grams of the TDI functionalized PEG 600 adipate was then combined with about 1 gram of this TMP. The mixture was heated to about 65° C. and mixed at about 50 rpm under static nitrogen for about 72 hours. This first component was transferred into syringes and stored in a dry box.

About 25 mg of bis(3-aminopropyl)amine was added to about 50 g of water as a solvent to form a dilute solution having bis(3-aminopropyl)amine at a concentration of about 0.05% by weight. About 0.1 ml of the dilute solution was contacted with about 0.1 ml of the first component to form a composition of the present disclosure.

The resulting composition was subjected to a lap shear test. Briefly, the lap shear test was conducted as follows. Shear forces of the adhesives were tested using a porcine intestine substrate cut to an area of about 1.5×4.5 cm. About 0.1 ml of the first component and 0.1 ml of the dilute solution described above were applied to the porcine tissue to form a composition of the present disclosure. The composition of the present disclosure was applied over an area of about 1.5×1 cm. Another piece of substrate was placed over the applied area of the composition of the present disclosure. A weight of about 20 grams was put on top of both substrates for about 30 seconds to ensure proper bonding of the composition of the present disclosure and to control its thickness. The composition of the present disclosure was left to cure for about 2 minutes. A tensiometer was used to measure the shear force exerted by the adhesive bond created between both substrates.

The composition of the present disclosure had a lap shear of about 1.4 kg. These results were excellent considering that conventional materials may only possess about 1.2 kg lap shear after a longer curing time, in some cases about 5 minutes or longer.

Various modifications and variations of the embodiments described herein will be apparent to those skilled in the art from the foregoing detailed description. Such modifications and variations are intended to come within the scope of the following claims.

What is claimed is:

1. A method comprising:
contacting at least one isocyanate-terminated component with a dilute solution comprising at least one amine at a concentration of from about 0.01 weight percent to about 0.5 weight percent of the solution at a temperature of from about 20° C. to about 40° C.; and
allowing the at least one isocyanate-terminated component and the at least one amine to react in situ thereby forming a cured biocompatible adhesive composition within from about 1 second to about 5 minutes after contact, wherein the at least one isocyanate-terminated component is of the formula:

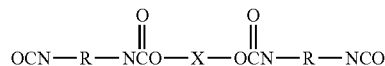

wherein X is a polyester selected from the group consisting of polybutylene adipate, polyethylene adipate, polyethylene terephthalate, and combinations thereof, R is an aliphatic or aromatic group, and the at least one isocyanate-terminated component has a molecular weight of from about 1000 g/mol to about 20000 g/mol.

2. The method of claim 1, wherein the amine is selected from the group consisting of bis(3-aminopropyl)amine, spermine, polyetheramine, trilysine, ethylenediamine, N-ethylethylenediamine, N,N'-diethylethylenediamine, butane-1,4-diamine, pentane-1,5-diamine, hexane-1,6-diamine, phenylene diamine, and combinations thereof having a molecular weight of from about 50 g/mol to about 500 g/mol.

3. The method of claim 1, wherein the solution comprises at least one solvent selected from the group consisting of water, ethanol, triethylene glycol, diglyme, triglyme, tetraglyme, polyethylene glycols, methoxy-polyethylene glycols, dimethylformamide, dimethylsulfoxide, dimethylacetamide, gamma-butyrolactone, N-methylpyrollidone, methyl ethyl ketone, cyclohexanone, diethylene glycol monoethyl ether acetate, diethylene glycol monobutyl ether acetate, diethylene glycol monomethyl ether, diethylene glycol monoethyl ether, diethylene glycol monobutyl ether, diethylene glycol monoisobutyl ether, diisobutyl ketone, diacetone alcohol, ethyl amyl ketone, ethyl lactate, tetrahydrofuran, ethyl acetate, isopropyl acetate, butyl acetate, isopropanol, butanol, acetone, and combinations thereof.

4. The method of claim 1, wherein the ratio of the amine to the at least one isocyanate-terminated component is from about 1:10 to about 10:1 w/w.

5. The method of claim 1, wherein the composition exhibits a lap shear of from about 0.8 kg to about 2 kg.

6. The method of claim 1, wherein the at least one isocyanate-terminated component and the at least one amine form the cured biocompatible adhesive composition within from about 30 seconds to about 2.5 minutes after contact.

7. A method comprising:
contacting at least one isocyanate-terminated component of the formula:

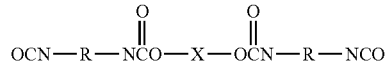

wherein X is a polyester selected from the group consisting of polybutylene adipate, polyethylene adipate, polyethylene terephthalate, and combinations thereof, R is an aliphatic or aromatic group, and the at least one isocyanate-terminated component has a molecular weight of from about 1500 g/mol to about 10000 g/mol, with a dilute solution comprising at least one amine selected from the group consisting of bis(3-aminopropyl)amine, spermine, polyetheramine, trilysine, ethylenediamine, N-ethylethylenediamine, N,N'-diethylethylenediamine, butane-1,4-diamine, pentane-1,5-diamine, hexane-1,6-diamine, phenylene diamine, and combinations thereof having a molecular weight of from about 50 g/mol to about 500 g/mol, at a concentration of from about 0.01 percent by weight to about 0.5 percent by weight of the solution, at a temperature of from about 20° C. to about 40° C.; and allowing the at least one isocyanate-terminated polyurethane and the at least one amine to react in situ to form a cured biocompatible composition within from about 1 second to about 5 minutes after contact.

8. The method of claim 7, wherein the solution comprises at least one solvent selected from the group consisting of water, ethanol, triethylene glycol, diglyme, triglyme, tetraglyme, polyethylene glycols, methoxy-polyethylene glycols, dimethylformamide, dimethylacetamide, gamma-butyrolactone, N-methylpyrollidone, methyl ethyl ketone, cyclohexanone, diethylene glycol monoethyl ether acetate, diethylene glycol monobutyl ether acetate, diethylene glycol monomethyl ether, diethylene glycol monoethyl ether, diethylene glycol monobutyl ether, diethylene glycol monoisobutyl ether, diisobutyl ketone, diacetone alcohol, ethyl amyl ketone, ethyl lactate, tetrahydrofuran, ethyl acetate, isopropyl acetate, butyl acetate, isopropanol, butanol, acetone, and combinations thereof.

9. The method of claim 7, wherein the ratio of the amine to the at least one isocyanate-terminated component is from about 1:10 to about 10:1 w/w.

10. The method of claim 7, wherein the composition exhibits a lap shear of from about 0.8 kg to about 2 kg.

11. The method of claim 1, wherein the at least one isocyanate-terminated component and the at least one amine form the cured biocompatible adhesive composition at a temperature of from about 25° C. to about 37° C.

12. The method of claim 7, wherein the at least one isocyanate-terminated component and the at least one amine form the cured biocompatible composition at a temperature of from about 25° C. to about 37° C.

13. The method of claim 7, wherein the at least one isocyanate-terminated component and the at least one amine form the cured biocompatible composition within from about 30 seconds to about 2.5 minutes after contact.

* * * * *